(12) United States Patent
Mueller

(10) Patent No.: US 10,688,145 B2
(45) Date of Patent: Jun. 23, 2020

(54) POULTRY FEED ADDITIVE

(71) Applicant: DELACON Biotechnik GmbH, Engerwitzdorf (AT)

(72) Inventor: Andreas Stefan Mueller, Wettin-Löbejün (DE)

(73) Assignee: DELACON Biotechnik GmbH, Engerwitzdorf (AT)

(*) Notice: Subject to any disclaimer, the term of this patent is extended or adjusted under 35 U.S.C. 154(b) by 0 days.

(21) Appl. No.: 15/754,864

(22) PCT Filed: Sep. 1, 2016

(86) PCT No.: PCT/EP2016/070588
§ 371 (c)(1),
(2) Date: Feb. 23, 2018

(87) PCT Pub. No.: WO2017/037157
PCT Pub. Date: Mar. 9, 2017

(65) Prior Publication Data
US 2018/0344795 A1    Dec. 6, 2018

(30) Foreign Application Priority Data
Sep. 1, 2015 (EP) .................... 15183332

(51) Int. Cl.
*A61K 36/48* (2006.01)
*A61K 36/53* (2006.01)
(Continued)

(52) U.S. Cl.
CPC ............ *A61K 36/53* (2013.01); *A23K 20/111* (2016.05); *A23K 20/121* (2016.05); *A23K 20/158* (2016.05); *A23K 40/30* (2016.05); *A23K 50/75* (2016.05); *A61K 31/58* (2013.01); *A61K 36/185* (2013.01); *A61P 3/00* (2018.01)

(58) Field of Classification Search
CPC ....................................................... A61K 36/48
See application file for complete search history.

(56) References Cited

U.S. PATENT DOCUMENTS

2009/0004308 A1    1/2009   Frehner et al.

FOREIGN PATENT DOCUMENTS

| EP | 1129627 A1 | 9/2001 |
| EP | 1419811 A1 | 5/2004 |
| WO | 2012113838 A1 | 8/2012 |

OTHER PUBLICATIONS

Da Silva et al., "Microencapsulation: concepts, mechanisms, methods and some applications in food technology," Ciencia Rural, Santa Maria, 44(7):1304-1311, Jul. 2014.*

(Continued)

*Primary Examiner* — Rosanne Kosson
(74) *Attorney, Agent, or Firm* — Maier & Maier, PLLC

(57) ABSTRACT

The use of a poultry feed additive composition which is a flowable mixture of phytogenic compounds including at least an oil component which is microencapsulated essential thyme oil, and a saponin component which is the saponin contained in particulate dried quillaja bark powder. The mixture contains at least 0.5% saponin component (w/w), and the oil component in an effective ratio of at least 0.2:1 (w/w, oil component per saponin component), for improving the feed conversion efficiency in antibiotic-free poultry production.

16 Claims, 5 Drawing Sheets

(51) Int. Cl.
　　　A23K 40/30　　　(2016.01)
　　　A23K 20/121　　(2016.01)
　　　A23K 50/75　　　(2016.01)
　　　A23K 20/111　　(2016.01)
　　　A23K 20/158　　(2016.01)
　　　A61P 3/00　　　 (2006.01)
　　　A61K 31/58　　　(2006.01)
　　　A61K 36/185　　 (2006.01)

(56) References Cited

OTHER PUBLICATIONS

International Search Report dated Dec. 8, 2016, in corresponding international application No. PCT/EP2016/070588; 5pgs.
Written Opinion dated Dec. 8, 2016, in corresponding international application No. PCT/EP2016/070588; 7pgs.
International Preliminary Report on Patentability dated Mar. 6, 2018, in corresponding international application No. PCT/EP2016/070588; 8pgs.
Extended European Search Report dated Feb. 24, 2016, in corresponding European application No. 15183332.4; 3 pgs.
Angkanapom K. et al., "Evaluation of homoarginine as a marker for the determination of endogenous amino acid concentrations in poultry excreta", 1997 British Poultry Science, 38:5, 577-585; 11 pgs.
Artursson P., "Epithelial Transport of Drugs in Cell Culture. I: A Model for Studying the Passive Diffusion of Drugs over Intestinal Absorbtive (Caco-2) Cells", 1990 Journal of Pharmaceutical Sciences, vol. 79 ( 6): 476-482; 7 pgs.
Biostrong 510, Mar. 29, 2015, XP002753640, URL:https://web.archive.org/web/20150329074022/http://www.delacon.com/Products/Poultry; 4 pgs.
Borgmann D. M. et al., "Identification of Patterns in Microscopy Images of Biological Samples Using Evolution Strategies", 2012 Proceedings of the 24th European Modeling and Simulation Symposium; 6 pgs.
Buchanan N. P. et al., "The Effects of a Natural Antibiotic Alternative and a Natural Growth Promoter Feed Additive on Broiler Performance and Carcass Quality", 2008 Journal of Applied Poultry Research, 17:202-210; 9 pgs.
Denyer S. P. et al., "Mechanisms of Action of Chemical Biocides", 1991 The Society for Applied Bacteriology Technical Series No. 27, Blackwell Scientific Publications, Oxford, 331-334; 5 pgs.
Hagemeister H. et al., "Chemical labelling of dietary protein by transformation of lysine to homoarginine: a new technique to follow intestinal digestion and absorption", Proceedings of the Nutrition Society, London, Meeting of May 20/21, 1985, vol. 44, 133A; 2 pgs.
Frank J. et al., "Inhibition of heme oxygenase-1 increases responsiveness of melanoma cells to ALA-based photodynamic therapy", 2007 International Journal of Oncology, 31(6):1539-1545; 7 pgs.

Hediger M. A. et al., "Molecular Physiology of Sodium-Glucose Cotransporters", 1994 Physiological Reviews, 74(4):993-1026; 35 pgs.
Kamphues J. et al., "Antibiotic Growth Promoting Feed Additives—An Assessment From the Point of View of Animal Nutrition", 1999 Übersichten Tierernährung, vol. 27, 1-28; 28 pgs.
Kikuchi G. et al., "Heme oxygenase and heme degradation", 2005 Biochemical and Biophysical Research Communications, vol. 338, 558-567; 10 pgs.
Knobloch K. et al., "Action of Terpenoids on Energy Metabolism", 16th International Symposium on Essential Oils 1986, Walter de Gruyter & Co., Berlin, 429-445; 17 pgs.
Lambert R.J.W. et al., "A study of the minimum inhibitory concentration and mode of action of oregano essential oil, thymol and carvacrol", 2001 Journal of Applied Microbiology, vol. 91, 453-462; 10 pgs.
Nazeer M. S. et al., "Effect of Yucca Saponin on Urease Activity and Development of Ascites in Broiler Chickens", 2002 International Journal of Poultry Science, 1 (6): 174-178; 6 pgs.
Nyachoti C. M. et al., "Significance of endogenous gut nitrogen losses in the nutrition of growing pigs: A review", 1997 Canadian Journal of Animal Science, 77(1): 149-163; 15 pgs.
Pahle T. et al., "Methodische Untersuchungen zur Bestimmung der Verdaulichkeit des Rohproteins beim Hühnergeflügel", 1983 Archlv für Tierernährung, 4/5, 363-370; 8 pgs.
Purser K. W. et al., "Effects of a phytogenic feed additive on performance in broilers", 2012 Poultry Science , 91(Suppl. 1):126; 6 pgs.
Scheuermann G. N. et al., "Phytogenic additive as an alternative to growth promoters in broiler chickens", 2009 Ciencia Rural, 39 (2):522-527; 6 pgs.
Schmitz M. et al., "Homoarginine Labeling is Suitable for Determination of Protein Absorption in Miniature Pigs", Journal of Nutrition 1991, 121: 1575-1580; 6 pgs.
Sikkema J. et al., "Mechanisms of Membrane Toxicity of Hydrocarbons", 1995 Microbiological Reviews, 59 (2), 201-222; 22 pgs.
Anonymous, "Trends in Animal Nutrition", Delacon, 2009, XP002753642, URL:http://www.google.de/url?sa=t&rct=j&q=&esrc=s&source=web&cd=1&ved=OahUKEwjR95vT387KAhVCxxoKHc9rCKcQFggdMAA&url=http%3A%2F%2Fwww.delacon.com%2Fdownload%2F%3Ffile%3D88&usg=AFQjCNHywG sT4ifin QU2Li9jqJCKjefw; 36 pgs.
Wald C., "Die Wirkung phytogener Zusatzstoffe in der Tierernährung", 2004 Lohmann Information, 2: 19-22; 4 pgs.
Wright E. M. et al., "The sodium/glucose cotransport family SLC5", 2004 Pflügers Archlv—European Journal of Physiology, 447:510-518; 10 pgs.
Yaghoobzadeh et al., "Effects of saponin and herb oil extracts mixed with feed on broiler performance and carcass characteristics", 2012 Poultry Science, 92 (E-Suppl.1):119-132, p. 363, XP055161204, URL:http://www.poultryscience.org/psa12/abstracts/119.pdf; 14 pgs.

\* cited by examiner

POULTRY FEED ADDITIVE

FIELD

The invention refers to poultry feed additive composition based on a flowable mixture of phytogenic compounds, in particular comprising an effective ratio of essential oils and saponins.

BACKGROUND

Zootechnical additives are commonly used to improve the nutritional value of an animal's diet. This category includes, among others, enzymes and certain phytogenics. Phytogenic (plant derived, natural, botanical) feed additives are well-blended compositions of special plant-based raw materials and plant derived and/or mineral-based carriers. For this purpose, essential and/or vegetable oils, as well as a vast range of highly active herbs and spices with special aromatic and appetizing properties may be used.

Because of its high problem-solving potential, a new generation of additives has taken a strong position in the animal nutrition industry, especially since the prohibition of antibiotic growth promoters in the EU. Phytogenic products may be used as a zootechnical additive, developed to improve the performance of animals, e.g. to improve the health of poultry and/or for profitable poultry production, especially for fattening and egg production. Phytogenic products are considered as natural alternative to the synthetic products that consumers want to avoid, including feed manufacturers, premixers and animal producers.

Saponins are amphipathic glycosides grouped phenomenologically by the soap-like foaming they produce when shaken in aqueous solutions, and structurally by their composition of one or more hydrophilic glycoside moieties combined with a lipophilic triterpene or steroid derivative. Feed additives including saponins have been reported to reduce ammonia emissions, which may be explained by the direct binding of ammonia to saponins and/or the inhibition of the bacterial enzyme urease (Nazeer et al. (Int. J. Poult. Sci. 2002; 1:174-178). Saponins extracted from plant material have also been described in combination with clay material to reduce gas emission in lifestock (WO2012113838A1).

EP1129627A1 describes a natural feed additive comprising an oligosaccharide-containing component, a saponin component obtained from a plant material originating from one or more plants selected from the genera *Yucca, Quillaja*, and others, or a synthetic material comprising corresponding substances identical to natural substances, and another component comprising an antibacterially active substance obtained from a plant material originating from one or more plants selected from citrus fruits, hops, grapes, and others, including plant material originating from *Saturela, Origanum, Thymus, Rosmarinus* or *Mentha*. According to specific examples, the feed additive is provided as a mixture of plant powders mixed in the dry state.

EP1419811A1 refers to microencapsulation of volatile substances, like essential oils, to improve storage stability and manufacturability of mixtures of plant extracts.

A commercially available product called Biostrong 510 (Delacon, Steyregg, Austria) has been provided as a phytogenic feed additive for poultry, which consists of a combination of microencapsulated essential oils and herbal substances aligned to the needs of high performing poultry.

Biostrong 510 compositions for use in conjunction with antibiotics are e.g. described in Scheuermann et al (Ciencia Rural 2009, 39(2):522-527), Purser et al. (Poultry Science 2012, 91(suppl. 1):126), and Buchanan et al. (J. Appl. Poultry Sci. 2008, 17:202-210), see also "Trends in Animal Nutrition" 2009, XP002753642. Such compositions were described to contain phytogenic compounds, yet with undefined saponin content and effect.

Yaghoobzadeh et al. (Poultry Science 2012, 92 (E-Suppl.1):119-132, P363 (abstract)) describe the effects of saponins and herb oil extracts mixed with feed on broiler performance and carcass characteristics.

Yet, there is a need to optimize the animal's performance and the increase of digestibility of nutrients. It is the object of the present invention to provide for a new poultry feed additive or feed composition with specific components to improve the animal's biophysical characteristics.

SUMMARY OF THE INVENTION

The object is solved by the subject matter as claimed.

According to the invention there is provided the use of a poultry feed additive composition which is a flowable mixture of phytogenic compounds comprising at least a. an oil component which is microencapsulated essential thyme oil, and b. a saponin component which is the saponin contained in particulate dried *quillaja* bark powder, which mixture contains at least 0.5% saponin component (w/w), and the oil component in an effective ratio of at least 0.2:1 (w/w, oil component per saponin component for improving the feed conversion efficiency in antibiotic-free poultry production.

Specifically, the effective ratio is in the range of 0.2:1-10:1, preferably in the range of 1:1-5:1, preferably in the range of 2:1-4:1.

Specifically, the mixture contains at least 0.2% (w/w) essential thyme oil, preferably at least 0.5, 1, 2, 3, 4 or 5%, e.g. up to 10% (w/w).

The composition as described herein specifically comprises the oil component in an amount ranging from 0.2% to 5% (w/w), and the saponin component in an amount ranging from 0.5 to 5% (w/w).

According to a specific embodiment, the *Quillaja* bark powder contains the saponin component in an amount ranging from 3 to 10% (w/w).

Further material which may be additionally used as saponin component may be selected from other plant species or plant parts containing saponins, e.g. selected from the group consisting of plant material derived from the botanical family Quillajaceae defining genus *Quillaja*, Agavoideae defining genus *Yucca*, Fabaceae defining genus *Trigonella*, Sapindaceae defining genus *Sapindus* (soapberry or soapnut), and in the closely related families Aceraceae (maples), Hippocastanaceae (horse chestnuts) and Sapotaceae. It is also found heavily in the seed hulls of Amaranthacea and in *Gynostemma pentaphyllum* (*Gynostemma*, Cucurbitaceae) in a form called gypenosides, and *ginseng* or red *ginseng* (*Panax*, Araliaceae) in a form called ginsenosides. Within these families, this class of chemical compounds is found in various parts of the plant: leaves, stems, roots, bulbs, blossom and fruit.

Specifically, the mixture contains at least 0.5% saponin component (w/w), preferably at least 1%, or at least 2%, e.g. up to 3, 4, or 5% (w/w).

Specifically, the composition additionally comprises further essential oils provided in a microcapsulated and/or free form, dried herbs, spices and further excipients, optionally including bulking and anti-caking agents.

According to a specific embodiment, the further essential oil is star anise oil, preferably at least 0.2% (w/w), or at least 0.5, 1, 2, 3, 4 or 5%, e.g. up to 10% (w/w).

Specifically, the essential thyme oil and optionally further essential oils, are microencapsulated by spray-drying an o/w emulsion. Such microencapsulation would provide for the long-term bioavailability of the essential oil concomitant with the bioavailability of the saponin component. The long-term, bioavailability is herein also called sustained release. Therefore, the composition of the invention provides for the sustained release of the active components, which are the oil component and the saponin component.

Microencapsulated essential oil provides for an oil component homogeneously mixed with other dry substances to provide for the flowable o/s (oil in solid) mixture or dispersion that may be stored at room temperature over a prolonged period of time of at least 18 months, preferably at least 2 years, e.g. in the powder form or pelleted form. For example, the composition of the invention may be pelleted with further nutritional feed substances to provide for pelleted feed compositions without significant losses of the essential oil even after long-term storage. Specifically, the composition may be provided as storage stable, pelletable preparation, with a stability of at least 18 months at room temperature, or a temperature of up to 25° C. Upon storage, at least 65% of the essential oil would remain in the mixture, preferably at least 70%, The composition as described herein preferably contains 20-60% (w/w) dried herbs. Amongst the preferred dried herbs there are powders of *angelica* root, anise, apple, artichoke, balm, barberry, basil, birch leaves, bitter orange, black currant, blackberry, blueberry, calamus, *cassia*, cedar, chamomile, chestnut, cimicifuga, cinnamon, citronella, clover, coltsfoot, common centaury, common nettle, dandelion, dill, elder flower, *eucalyptus*, fennel, gentian, ginger, ginko, grape seed, grape seeds, grapefruit, greater celandine, green tea, hawthorne, hop, horseradish, horsetail, hyssop, ipecac, lemon, lemon balm, lemongrass, licorice, lovage, maca, marigold, marjoram, marshmallow, mint, mistletoe, mugwort, muira puama, oak wood, olive leaves, orange, oregano, parsley, *passiflora*, peppermint, pine needle, purple coneflower, *psyllium*, quassia, quebracho, *quillaja*, raspberry leaves, ribwort, rose, rosemary, rue, rose hips, saflor, sage, sandalwood, savory, Siberian *ginseng*, soapwort, st. johnswort, star anise, taiga root, tea, thyme, tormentil, valerian root, wormwood, yarrow, yohimbe bark.

The composition may further include dried spices, e.g. 1-15% (w/w), like allspice, camphor, caraway, cardamom, cayenne pepper, clove, coriander, cumin, *curcuma*, fenugreek, garlic, juniper berry, nutmeg, onion, paprika, pepper, turmeric Further excipients may be used which are bulking and anti-caking agents, e.g. in an amount ranging 20-60% (w/w), organic sources like wheat bran, rice bran or other grain brans, modified starch, lactose or dextrose and anorganic sources like silicon dioxide, limestone orbentonite.

According to the invention, there is further provided the composition as described herein, which is contained in a feed product, preferably at a dose of at least 100 mg per kg feed product, optionally provided in the pelleted form. Preferred doses are at least 150, optionally at least 200 or 250 mg/kg, or optionally higher amounts, e.g. up to 750 mg/kg.

For example, the feed additive composition is admixed to a feed material, e.g. bruised grain, by-products from the alkohol production based on grains, oil seeds like rapeseed, linseed, soybean and by-products from the oil production like soybean meal, rapeseed meal, rapeseed cake, linseed meal, linseed cake or by-product from the fish and meat processing industry like fish meal, meat meal, meat and bone meal, feather meal, blood meal and hydrolyzed animal derived proteins and mineral premixtures, and optionally pelleted by a process of compressing or molding a material into the shape of a pellet.

According to the invention, there is further provided the use of the feed additive composition of the invention or the feed product of the invention, for improved feed conversion in poultry. Specifically, the improved feed conversion is determined by an increased ileal nutrient digestibility or a decreased feed conversion rate, e.g. determined by the respective in vitro or in vivo models.

Specifically, the material is used as digestibility and performance enhancer, e.g. according to the definition of Regulation (EC) 1831/2003, in poultry for fattening or laying or breeding, to point-of-lay.

According to the invention, there is further provided a method of feeding a poultry animal with a feed product of the invention, wherein said feed results in an improvement in one or more of said animal's biophysical characteristics when compared to the equivalent use of a feed product that does not comprise the feed additive composition of the invention.

According to the invention, there is further provided a method of feeding a poultry animal with a feed product comprising administering the composition as described herein with an antibiotic-free diet, wherein said feed results in an improvement of the feed conversion efficiency.

Specifically, said improvement results in an increase in (average) daily weight gain, preferably of at least 1.0% or at least 2.0%, over a period of 35 days, when the composition is dosed at an amount of at least 100 mg per kg feed product.

Specifically, said improvement results in a decrease in the feed conversion ratio, preferably of at least 1.5% or at least 2%, over a period of at least 35 days, when the composition is dosed at an amount of at least 100 mg per kg feed product.

Specifically, said improvement results in an increased ileal protein digestibility, preferably of at least 1% over a period of at least 35 days, when the composition is dosed at an amount of at least 100 mg per kg feed product.

Relative concentration of the essential oil component A (fold change compared to the dietary dose level)

Figure 3:
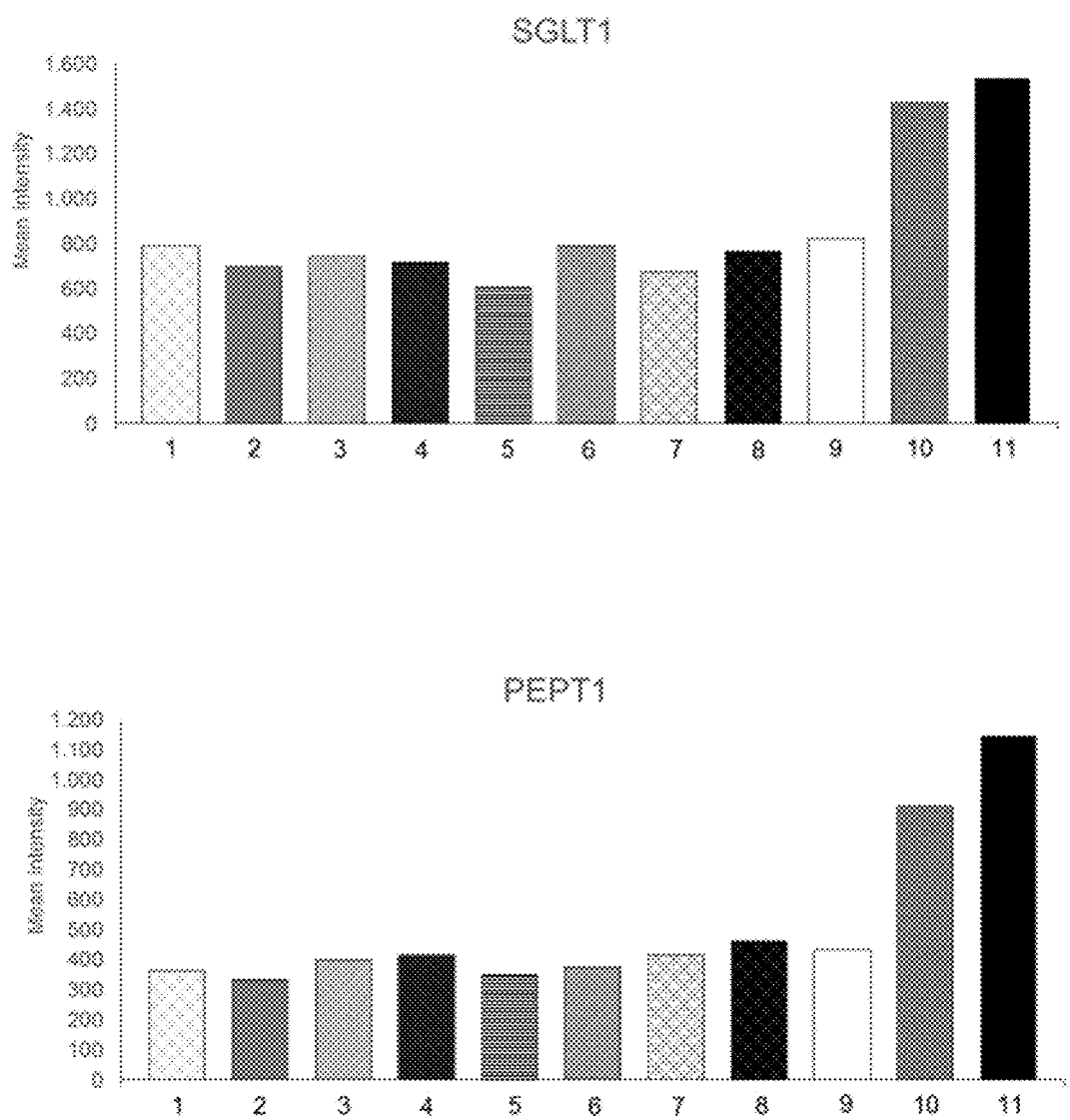

1: 0-control; 2: 0.13-fold; 3: 0.25-fold; 4: 0.50-fold; 5: 1.00-fold; 6: 2.50-fold; 7: 5.00-fold; 8: 7.50-fold; 9: 10.0-fold; 10: 17.5-fold; 11: 25.0-fold FIG. 3: dose-depending effect of the saponin component B on membrane recruitment of sodium-dependent glucose transporter SGLT1 and di- and tripeptide transporter PEPT1 in CaCo2-cells.

Description of bars:

Relative concentration of the saponin component B (fold change compared to the dietary dose level)

Figure 4:
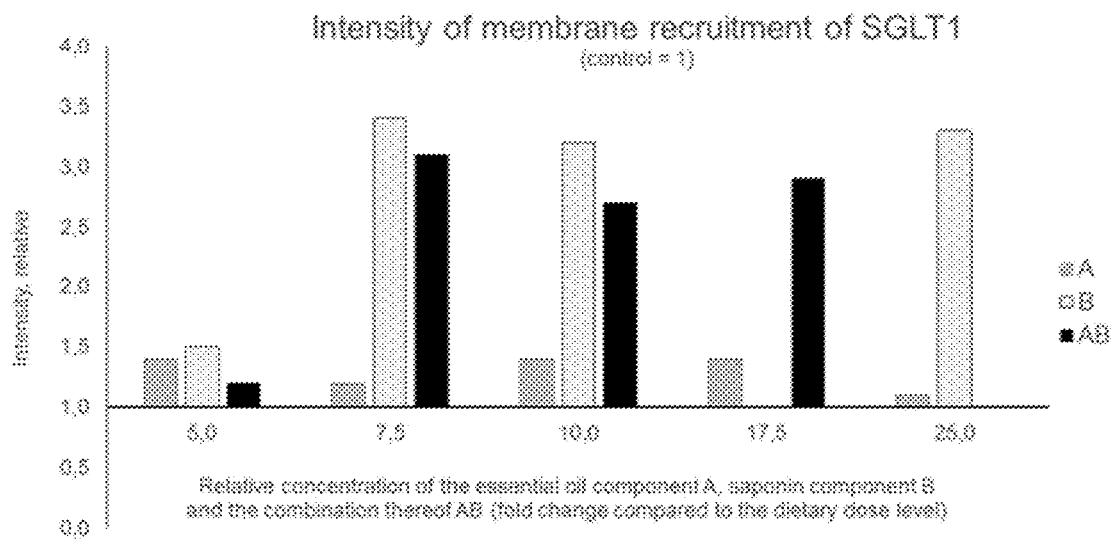
Figure 4:
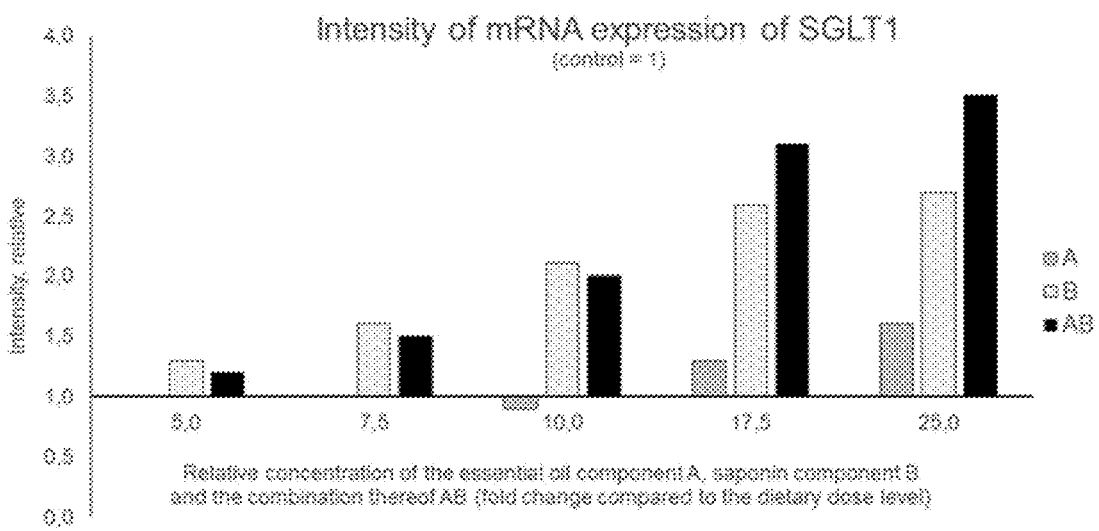

1: 0-control; 2: 0.13-fold; 3: 0.25-fold; 4: 0.50-fold; 5: 1.00-fold; 6: 2.50-fold; 7: 5.00-fold; 8: 7.50-fold; 9: 10.0-fold; 10: 17.5-fold; 11: 25.0-fold FIG. 4: dose-depending effect of the essential oil component A, the saponin component B and the combination thereof AB, on membrane recruitment and mRNA expression of the epithelial sodium-dependent glucose transporter SGLT1 in CaCo2-cells.

Figure 5:
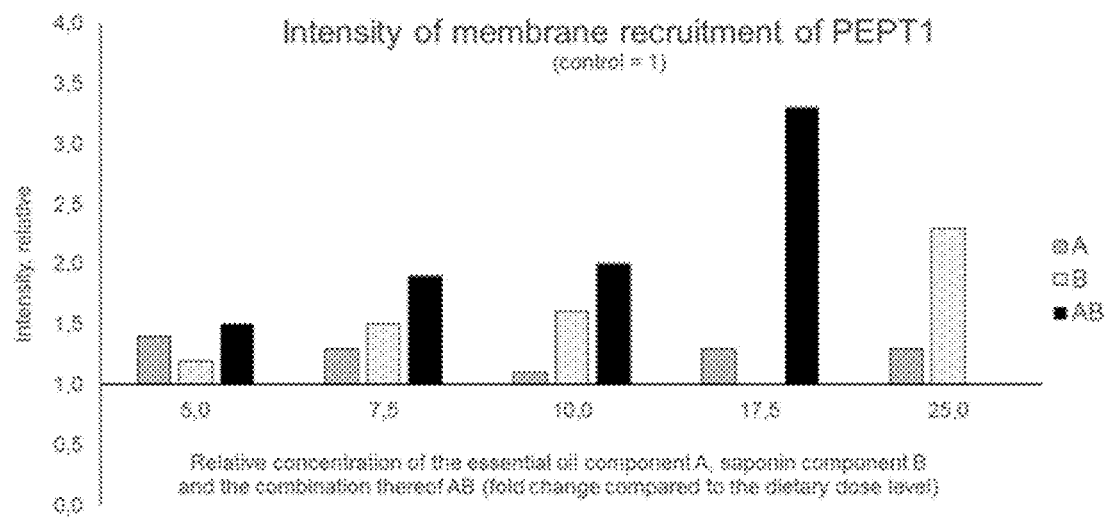
Figure 5:
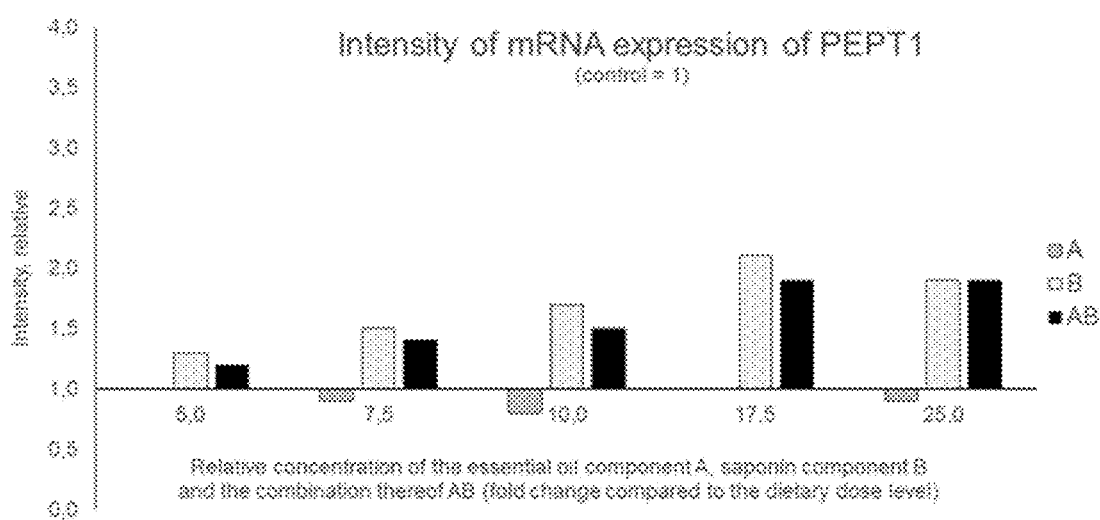

FIG. 5: dose-depending effect of the essential oil component A, the saponin component B and the combination thereof AB, on membrane recruitment and mRNA expression of the epithelial di- and tripeptide transporter PEPT1 in CaCo2-cells.

DETAILED DESCRIPTION

Specific terms as used throughout the specification have the following meaning.

The term "antibiotic-free" as used herein with respect to feeding an animal, a diet or a feed product, shall refer to the feeding of an animal with a feed product devoid of antibiotics. Though the animal may have been treated with antibiotics upon veterinary prescription, the regular diet would not contain additional antibiotics as growth enhancer. Thus, accumulation of such harmful substances as antibiotics and the like in persons who have consumed the meat or eggs of poultry is prevented. The compositions as described herein effectively improve the food conversion thereby substituting antibiotics in feed products. Thus, it is possible to increase the productivity of meat of good quality.

The term "biophysical characteristics" of an animal like poultry is herein understood as the biotic and abiotic function of an animal, or population, and includes particularly the factors that have an influence in their survival, development and evolution, in particular including factors improving the feed conversion efficiency in animals, e.g. as determined by in vitro or in vivo models. Such factors include e.g. intestinal membrane permeability, nutrient digestibility, ileal protein digestibility, nutrient transport, antimicrobial or antioxidative effects.

The "feed conversion efficiency" as herein understood specifically refers to a measure of an animal's efficiency in converting feed mass into increased body mass (e.g. muscle or egg mass). The efficiency may be determined as the feed conversion rate, which is the mass of the food eaten divided by the body mass gain, all over a specified period. For example, an animal being fed with a feed additive designed for improved feed conversion efficiency may consume less food than an animal that received feed without such feed additive, producing a similar amount of meat. Typically, the feed conversion rate of poultry is in the range of 1.2 to 2.5, depending on the genetic breed.

An improval in the feed conversion rate or a factor influencing the feed conversion efficiency may be determined, if the feed conversion rate or the factor is decreased e.g. by at least 2%, preferably at least 2.5%.

A 'synergistic effect' of the oil component and the saponin component in the feed additive composition of the invention is specifically determined, if the effect of the mixture provided in the effective ratio is unexpectedly higher than the effects that are obtained with the individual components.

There are direct factors influencing the feed conversion efficiency, e.g. including nutrient digestibility, ileal nutrient or protein digestibility, intestine membrane permeability, nutrient transport systems of the brush border membrane, or indirect factors, such as those improving the health status of the animal and reducing the energy and protein demand for immune reactions, including antimicrobial effects.

The term "intestine membrane permeability" is herein understood as a factor determining intestinal absorption of nutrients, such as by passing though a cellular membrane of the intestine. Such biophysical characteristics may be determined by the ex vivo model employing epithelial colorectal cells to test a change in permeability upon contact with specific substances. The term "nutrient transport systems" is herein understood as an active transport of nutrients, including e.g. glucose, peptides and amino acids, from the lumen of the small intestine across the brush border membrane into the enterocytes. Such nutrient transport systems are specific enzymes, including e.g. the sodium-dependent glucose transporter (SGLT1) and small peptide and amino acid transporter (PEPT1). Such biophysical characteristics may be determined by the ex vivo model employing epithelial colorectal cells to test a change in gene expression of the SGLT1 transporter enzyme upon contact with specific substances. The term "antimicrobial effects" as understood herein refers to the possible bacteriostatic effects of bacteria that are possibly pathogenic to monogastric animals, including poultry. Such biophysical characteristics may be determined by the ex vivo model employing bacterial cells to test a change in bacterial cell growth upon contact with specific substances.

The term "component" with regard to a composition is herein understood as a part of a composition, which may include one or more further components and excipients. The feed additive composition of the invention comprises at least the oil component and the saponin component, but may further include biological components, primarily phytogenic components and excipients, including e.g. anorganic excipients.

The oil component as used according to the invention is specifically provided in the microencapsulated form. Typically, the microencapsulation of the essential oil provides for its isolation from its surroundings, e.g. isolating the oils from the deteriorating effects of saponins in the aqueous phase, e.g. in the gastrointestinal environment, retarding evaporation of the volatile oil, protection against friction and evaporation due to humidity and high temperature during the feed processing (pelleting) or improving the handling properties of the sticky material. In addition, the rate may be effectively controlled at which the oil leaves the microcapsule, as in the sustained or controlled release of the oil in the gastrointestinal tract, aiming at providing an effective amount of the active components in the intestines. Thereby the release of the oil and saponin component may be achieved in a synchronized way to achieve the synergistic effects in vivo.

A wide range of materials and methods may be used for encapsulation to create the degree of durability and method of release suitable to the intended use. Non-limiting polymeric exemplary materials suitable for use with the microencapsulation of oil may include natural polymers of eukaryotic or prokaryotic origin, e.g. including starch hydrolysates, like dextrins, modified starch, *Gummi Arabicum*, alginates, cellulose derivatives, like hydroxypropylcellulose, Na-carboxycellulose, methylcellulose, ethylcellulose, animal or plant proteins or protein hydrolysates, like gelatin, collagen, egg yolk, wheat protein, casein, milk protein, soy protein, pea protein, or mixtures thereof. Various physical and chemical methods of microencapsulation may be used, depending on the oil and the desired polymeric shell coating to be used. Conveniently, the essential oil is encapsulated by dehydrating an o/w emulsion by any suitable means, including spray drying, freeze drying, fluid bed drying, tray drying, adsorption, and combinations thereof. Preferably, the microencapsulated oil is produced by spray-drying an emulsion having an aqueous phase as defined above containing a polymeric encapsulation agent. The spray-drying parameters are dictated by the physical characteristics desired in the final microencapsulated oil. Such physical parameters include particle size, flow and water content.

A preferred method employs the preparation of an o/w emulsion including the oil, the polymer and a solubilizer or detergent, followed by spray-drying at controlled temperature to obtain a flowable dry oil component consisting of microencapsulated oil. An exemplary method is described in EP1419811A1.

The microencapsulated oil typically has good flowability and the oil can be distributed homogeneously throughout the composition. Conveniently, the oil component is a powder. Any suitable additive may be added to the microencapsulated oil, e.g. a flow agent such as silicon dioxide, to increase the flowability of the microencapsulated oil.

The saponin component as used according to the invention is specifically a plant material comprising the saponin in the specified amount, which is provided in the particulate dry powder form.

The term "powder" as used herein is specifically understood as a flowable material comprising a plurality of particles. The particles may have a smooth outer surface and/or a flattened morphology. In certain embodiments, the particulate plant material is a beige to dark brown powder with a characteristic smell.

The particulate plant (*quillaja* bark) material used herein is specifically obtained by grinding dry plant material to obtain a specific particle size, e.g. corresponding to flowable material, e.g. $SiO_2$ (powder), a flour and/or semolina.

The particles may have an average largest dimension of 250-500 □m. The typical particulate material has a particle size of min 95% below 500 □m. Preferably, the particulate plant material has a mean particle size of 100-350 □m.

The plant powder material can be derived from various portions of the plant, specifically fibrous plant materials may be used, e.g. including bark, roots, stalks, stems, leaves, flowers, seeds, or combinations thereof. Exemplary materials are derived from Quillajaceae, Agavoideae, Fabaceae, Sapindaceae, Aceraceae, Hippocastanaceae, Sapotaceae, Amaranthacea, Cucurbitaceae or Araliaceae, and combinations thereof. Of interest are plant materials derived from *Quillaja* bark and *Yucca*.

In addition, saponins can be used in a concentrated form, e.g. extracted from the material described above. According to a specific embodiment, the saponin component additionally comprises saponins of plant extracts.

The saponin content in the particulate plant material may be determined by conventional methods, e.g. by determining the foam index.

The dry saponin component or the feed additive composition may e.g. be analysed for its capability of providing the desired amount of foam, employing a method as described in the Examples section. The volume of the foam layer determined in this fashion is the "foam index" of the test material, which foam index is correlated to the saponin content.

The moisture content of the particulate plant material or the feed additive composition of the invention is typically less than 12%, preferably less than 8%.

The term "excipients" as used herein shall specifically refer to additive components commonly used in feed compositions, e.g. phytogenic and/or anorganic feed additive components. Specifically, the feed additive and its additive components are understood as products used in animal nutrition for purposes of improving the quality of feed, or to improve the animals' performance and health. Feed additives are typically carefully selected which have no harmful effects, on human and animal health and on the environment.

In this regard, the term "feed" typically refers to any mixture of animal feed ingredients providing energy and nutrient requirements, e.g., protein, fat, carbohydrates, minerals and micronutrients. For example, a daily intake of poultry feed is typically between 50-250 g/head and day for a broiler for fattening.

The feed additive composition of the invention may specifically include excipients, such as further essential oils, dried herbs, spices and further excipients, including colors, flavoring substances, preservatives, or any substance needed to formulate the composition to the desired form, such as bulking, anti-caking agents, diluents, fillers, binders, disintegrants, adsorbents, or granulating agents. Typical excipients are for example rosemary leafs, juniper berries, *psyllium* hulls, wheat bran, limestone, $SiO_2$ or bentonites.

The term "flowable" as used herein shall specifically refer to a mixture of components in the powder form, including e.g. particulate material, which may flow. For example, a flowable mixture may flow through a funnel or hopper into another container under the influence of gravity. In the present invention, a flowable powder mixture is suitable for use with a device for mixture with feed material and pelleting. The term "flowable" is well known in the food and feed industry and has a clear meaning to the person skilled in the art.

A flowable mixture has several advantages in use, particularly on an industrial scale. The mixture may be handled, stored and transported relatively easily and energy-efficiently, as compared with, for example, solid materials that are not flowable. This advantage is particularly important in combination with the ability to avoid a liquefying step in the pelleting process.

The flowable mixture as used herein is specifically comprising the oil and saponin component and optionally other components and excipients, wherein the components are all mixed together without the inclusion of any substantial amount of liquid to form a dry mixture, which is optionally ground into a flowable, preferably pelletable powder.

The term "sustained release" as used herein shall specifically refer to the composition which provides for the gastric-retentive system to provide for nutrient delivery to the intestine. The task of the sustained release feed additive composition is specifically the controlled release of the active components in the conditions of the intestines, where the feed conversion efficiency is mainly influenced. Administrating of the active components requires the use of an appropriate vehicle for bringing an effective amount of the active components into the desired place of action. The desired level of controlled or sustained release will vary, depending upon the ratio of the components employed, the physical properties of the composition, the method of mixing of the components, and the like. Additional additives may also be present which may modify the characteristics of the mixture and its release properties.

The microencapsulated nature of the oil component and the saponin component, which is a particulate plant powder, specifically provide for the phytogenic system that inherently improves the sustained release properties of the active components, e.g. in the effective ratio to improve the biophysical characteristics as required. The composition comprises the components which do not dissolve or dissolve only poorly in the stomach. The components of the feed additive composition may be sufficiently provided to the intestine and/or colon, so that both components may concomitantly act on the biophysical characteristics.

Thus, it is possible to obtain synergistic sustained release effects in the intestines when the oil component and the saponin component are provided in the effective ratio, which is capable of improving one or more of the biophysical characteristics as described herein.

The effective ratio is specifically based on effective amounts of the components of the composition of the invention, which provide the requisite activity in the treated animal for the desired period of time.

It turned out that the effective ratio of the oil component to the saponin component achieved surprisingly improved biophysical characteristics, as determined by in vitro and/or in vivo models. Though oil and saponins were thought to bring about contradicting effects, the specific texture as microcapsules homogeneously distributed with solids (o/s dispersion) and particulate plant material containing the saponing components, and the specific ratio of both components turned out to effectively enhance the feed conversion efficiency in poultry. While saponins were known to act as foaming and emulsifying agent in aqueous solutions, essential oils have a very limited solubility in water.

In the prior art, the essential thyme oil was also used as antibacterial oil, which would act upon its hydrophobicity, which enables it to partition in the lipids of the bacterial cell membrane and mitochondria, disturbing the structures and rendering them more permeable (Knobloch et al. 1986); and the high amount of antioxidative phenolic compounds such as carvacrol and thymol is correlated with the strongest antibacterial properties against food borne pathogens (Lambert et al. 2001). It seems reasonable that their mechanism of action would therefore be similar to other phenolics; this is generally considered to be the disturbance of the cytoplasmic membrane, disrupting the proton motive force (PMF), electron flow, active transport and coagulation of cell contents (Denyer and Hugo, 1991b; Sikkema et al., 1995; Davidson, 1997). Antimicrobial activities have already been discussed as a key factor for performance enhancing effects (Kamphus and Hebeler 1999) in vivo. Wald (2004) investigated the antimicrobial effects in vivo of the essential oils that were selected for their antimicrobial effects in vitro. Antimicrobial effects were described only if the essential oil was dosed 10-1000 times of the antibiotic positive control. A performance enhancing effect in vivo was not determined.

It was therefore the more surprising that the essential oil and the saponin could concomitantly act in the intestines, e.g. to improve the feed conversion efficiency, e.g. with essential thyme oil doses far below the amounts which were so far discussed to enhance the animal's performance.

The term "poultry" as used herein shall specifically refer to domesticated fowl kept primarily for meat and eggs; including birds of the order Galliformes, e.g., the chicken, turkey, guinea fowl, pheasant, quail, and peacock; and Anserigormes (swimming birds) e.g., the duck and goose.

The poultry may be fed with the same feed composition throughout the growth period, or at least during a period of at least 3 weeks, preferably at least 4 weeks to improve the efficiency of feed use or feeding efficiency, e.g. output per unit of feed. Significant differences may be found between control and experimental treatments in final body weight and weight gain at the entire growth periods till 28 days after hatching. While the feed intake may be almost equal between treatments, the feed efficiency, i.e. g feed/g weight gain may be significantly better for poultry and specifically chicken fed with the feed additive composition of the invention.

A specific example of a feed additive composition of the invention relates to a new composition and its formula.

Further examples are directed to the determination of the biophysical characteristics to show the synergistic action of the active components of the composition.

The foregoing description will be more fully understood with reference to the following examples. Such examples are, however, merely representative of methods of practicing one or more embodiments of the present invention and should not be read as limiting the scope of invention.

EXAMPLES

Example I: New Poultry Feed Additive

The composition contains the following ingredients, admixed to a dry flowable mixture. Whereas the oil component is microencapsulated thyme oil, the saponin component is *Quillaja* bark powder.

TABLE 1

New poultry feed additive

| Ingredients | Content (%, w/w) |
| --- | --- |
| Essential oils of thyme and star anise | ≥7.4% |
| Thymol | 0.2-0.4% |
| Anethole | 4.0-5.0% |
| *Quillaja* bark powder | ≥20.0% |
| Saponins | ≤2.3% |
| Crushed, dried herbs & spices | 25-30% |
| Excipients | To 100% |

This new poultry feed additive formula contains an effective ratio of 1.5:2.2 (w/w oil component per *Quillaja* saponin component). The formula is tested in the test systems described below to show a synergistic effect of the oil component, herein named component "A", and the saponin component, herein named component "B", wherein the synergistic effect is more than the sum of the effect of the individual components: AB>A+B.

Example II: Description of Relevant Analytical Methods and Trial Methologies

Description of the analytical active substance evidence
1. Essential oil content
2. Thymol content
3. Saponins—foam index
4. Micro-encapsulation
Description of trial methodologies
5. In vitro evaluation of nutrient transport
6. In vivo validation of nutrient transport systems of the brush border membrane and its relevance for animal performance
  a. Ileal nutrient digestibility in broilers
  b. Evaluation of metabolic and signaling pathway in liver and jejunum
  c. Feed conversion efficacy in broilers
Description of the Analytical Active Substance Evidence
1. Essential Oil Content The essential oil content in herbs & spices as well as the products thereof, including the new formula of Table 1, or other products of the present invention, can be analyzed by the method No. 2.8.12 described in the European Pharmacopoeia (Version 7.5).
Test Principle The determination of essential oils is carried out by steam distillation in a special apparatus in the conditions described below. The distillate is collected in the graduated tube, using xylene to take up the essential oil; the aqueous phase is automatically returned to the distillation flask.

Instruments 250 ml, 500 ml or 1.000 ml round bottom flask with ground joint (NS 29)
ground joint clamps
heating mantle
funnel
scale
beakers
graduated pipette
graduated cylinder
boiling stones
disposable gloves
goggle
apparatus for determination of essential oils in drugs Chemicals Xylene puriss. p.a., Reag. ACS (33817; Sigma-Aldrich; GER)
Anti-foaming agent "Silicon-Antischaum US" (Brelu; AUT)
HCl 0.1 mol/l (9.8 ml of HCl 32% per liter of distilled water)

Determination of Essential Oils a) With xylene: (Some products, containing high density Oils, need the use of xylene)

For that purpose the plug "K'" has to be removed and 0.5 ml xylene has to be added through the opening.

After 15 minutes of distillation the heating mantle is switched off. The water stops boiling after approx. 10 minutes.

The xylene is drained into the measuring tube. After additional 10 minutes the volume of the xylene is ascertained. Then the valve has to be opened again.

Further procedure continues at "b.) without xylene", see description below.

b) Without xylene: (standard procedure)

The prescribed amount of the sample is put into the round bottom flask, the distillation medium and maybe some anti-foaming agent are added and then the distillation is started. If the same round bottom flask is used for the sample distillation as for the "cleaning-distillation" it has to be proved, that the flask is cooled down to room temperature before adding the sample.

To collect the total essential oil content, the cooling has to be switched off, after the prescribed distillation time.

After the steam reaches the bottom of the cooler, the cooling is enabled again and the heating mantle is switched off.

When the water stops boiling (after approx. 10 minutes) the organic phase is let off into the measuring tube and after additional 10 minutes the volume of the organic phase is measured.

Calculation of Essential Oil Content a) With xylene:

From the measured total volume of the organic phase the volume of the added xylene has to be subtracted. The difference is the total amount of the essential oil in the sample.

$$C\ [\%] = \frac{(V_2 - V_1)}{EW} \times 100$$

C . . . total content of essential oil in the sample in [%]
V1 . . . volume of the added xylene in [ml]
V2 . . . volume of the organic phase in [ml]
EW . . . taken amount of the sample in [g]

b) Without Xylene:

$$C\ [\%] = \frac{V}{EW} \times 100$$

C . . . total content of essential oil in the sample in [%]
V . . . volume of the organic phase in [ml]
EW . . . taken amount of the sample in [g]

2. Thymol Content

The quantitative detection of the lead substance Thymol in the essential thyme oil was done by a Gas Chromatograph-Mass Spectometry (GC-MS).

Test Principle

GC is a common type of chromatography used to separate and analyze volatile compounds without decomposition. The gases are analyzed as they interact with the column walls, which have been coated with different stationary phases. This coating results in the compounds eluting at different times, called the retention time for each compound. These compounds are then further analyzed by comparison with calibrated standard gases.

Instruments

Apparatus: GC VARIAN 3800
Capillary column:
DB 5, length: 30 m, I.D.: 0.25 mm
film thickness 0.25 μm
Injection:
Injection volume: 1 μl
Split: 1:50
Vials: 2 ml GC Vial
Detection: MS
Ion Trap 220° C., 10 μA ion current, target 20.000, multiplier 1850 V, 0.25 scans/sec
mass range: m/z: 35-350,
Temperature-program:
Injector-Temperature 180° C.
Heating rate 40° C.: 1 min
40° C.-220° C.: 20° C./min
Carrier gas: He 1 ml/min constant flow Chemicals Thymol p.a.
Ethanol p.a.
Biphenyl p.a.

Determination of Thymol Content in Premixture

Quantitative determination of Thymol by using an internal standard: Biphenyl

Thymol standard solutions

Thymol concentration: 1-100 μg/ml (Ethanol)
Biphenyl concentration in the standard solutions: 20 μg/ml Preparation of sample solution 10 ml GC vial: 60 mg premix and in addition 10 ml Ethanol extraction: 1 hour ultrasound, room temperature, filtered: 0.2 μm Filter Biphenyl concentration in the sample solution: 20 μg/ml 3. Saponins—Foam Index Saponins are a class of chemical compounds, based on a broad variety of aglycons (sapogenin) bound with a different number of saccharides. Sapogenins are either steroids, steroid alkaloids (nitrogenous steroids) or triterpenes. One characteristic of saponins is their ability to produce foam in water solutions. The foam index is a simple test to determine the presence of saponins in premixtures and compound feed.

Test Principle

Of the sample to be examined, an aqueous solution is prepared which is shaken vigorously in a volumetric flask. The foam index is obtained from the height of the foam standing over the liquid in centimeters.

Instruments
scale
beaker
stirring rod
500 ml graduated cylinder
funnel
folded filter paper
ruler
10 ml graduated pipette
disposable gloves Determination of Saponins in Premixtures 5 g of sample material are mixed with 95 g of tap water and stirred well with a glass rod.

This suspension is now left to soak for at least 12 hours, ideally overnight. After sufficient soaking time, the suspension is stirred and filtered through a fluted filter.

350 ml of cold tap water (T: 18° C.) is placed in a graduated cylinder (500 ml) and mixed with 5 ml of the filtrate. The cylinder is closed with a parafilm and shaken vigorously for 30 sec. horizontally. After another 30 sec. standing time, the foam height is determined in cm (foam above the liquid surface). The foam index is calculated as the mean of a duplicate determination.

Calculation of Saponins Content in Premixtures

The foam index is an instrument to estimate the saponin content. An ensurance of the required minimum content is possible, but not a statement on the exact saponin content. The conversion from foam index to saponin content is not linear and only possible within saponin contents of 0.5% to 5%.

$$\text{Saponin content [\%]} = \frac{\text{foam index [cm]}}{\text{conversion factor}}$$

Conversion Factor:

| Conversion factor | Foam index | Saponin content |
|---|---|---|
| 6.0 | 3 cm | 0.5% |
| 4.0 | 4 cm | 1.0% |
| 2.5 | 5 cm | 2.0% |
| 2.0 | 6 cm | 3.0% |
| 1.5 | 7 cm | 5.0% |

Evidence of Micro-Encapsulation of Essential Oils

4. Micro-Encapsulation

To ensure a slow and steady release of essential oils in the digestive tract, the essential oils used are subjected to a specific micro-encapsulation. The micro-encapsulation is characterized by the stability in different solvents.

Chemicals
Deionized water
Synthetic gastric juice

| NaCl: | 290 | mg/100 ml |
|---|---|---|
| KCl: | 70 | mg/100 ml |
| $KH_2PO_4$: | 27 | mg/100 ml |
| Pepsin: | 100 | mg/100 ml |
| Mucin: | 300 | mg/100 ml |
| HCl: | | adjust to pH 2 |

Synthetic intestinal juice

| KCl: | 30 | mg/100 ml |
|---|---|---|
| $CaCl_2$: | 50 | mg/100 ml |
| $MgCl_2$: | 20 | mg/100 ml |
| $NaHCO_3$: | 100 | mg/100 ml |
| Trysin: | 30 | mg/100 ml |
| Pankreatin: | 900 | mg/100 ml |
| Bile, lyophilized: | 900 | mg/100 ml |
| Urea: | 30 | mg/100 ml |

Instruments
microscope

Determination of Micro-Encapsulation in Deionized Water

The structure of the encapsulated particle is evaluated microscopically. With the subsequent addition of the deionized water, the encapsulation structure of the particles is maintained for at least 30 minutes.

Determination of Micro-Encapsulation in Synthetic Gastric Juice

The structure of the encapsulated particle is evaluated microscopically. With the subsequent addition of synthetic gastric juice (pH 2), the encapsulation structure of the particles is maintained for 2 hours and releases the essential oils afterwards.

Determination of Micro-Encapsulation in Synthetic Intestinal Juice

The structure of the encapsulated particle is evaluated microscopically. With the subsequent addition of synthetic intestinal juice (pH 7.5), the encapsulation structure of the particles is maintained for 2 hours and releases the essential oils afterwards.

Description of Trial Methodologies

5. Feed Conversion Efficiency in Broilers

In Vitro Evaluation of Nutrient Transport

The capacity for nutrient transport of the brush border membrane is essential to increase the nutrient efficiency of the animal. Membrane transporters mediate the transport of nutrients across the cell membranes, thus enable an efficient cellular nutrient transport.

To evaluate the effects of the essential oil component A, the saponin component B and the combination thereof AB, on the nutrient transport system of the brush border membrane, a CaCo-2 cell model was used to measure the fluorescence intensity values, indicating the presence of nutrient transporters proteins. For the observation the most relevant transporters were selected, mediating the nutrient transport form gut lumen across the cells of the brush border membrane, SGLT1 and PEPT1.

Glucose is transported from the lumen of the small intestine across the brush border membrane into the enterocyte primarily by the sodium-dependent glucose transporter, SGLT1 (Hediger and Rhoads, 1994; Wright and Turk, 2004).

The transporter PEPT1 is localized to the brush border membrane of the intestinal epithelium and mediates the uptake of di- and tripeptides from the lumen into the enterocytes. This protein plays an important role in the uptake of dietary proteins. PEPT1 is also known as solute carrier family 15 member 1 (SLC15A1), a protein that in humans is encoded by SLC15A1 gene.

Cultivation of the CaCo-2 Cell Line

Human CaCo-2 cells were purchased from DSMZ (Braunschweig, Germany). CaCo-2 cells were cultured in MEM with Earle's salts medium, supplemented with 10% FBS, 1% penicillin/streptomycin and 0.1% 2-mercaptoethanol. Cells were grown at 37° C. in a humidified incubator (≥95%) with 5% $CO_2$. CaCo-2 cells for fluorescence microscopy experiments were seeded at 150.000 cells/well in a 96-well plate with DMEM supplemented with 10% FBS, 1% penicillin/streptomycin and 1% non-essential amino acids for 24 hours. Media were replaced with Enterocyte Differentiation Medium supplemented with 10% FBS, 1% penicillin/streptomycin and MITO⁺ Serum Extender and changed at least every day and the experiment was carried out on day 5 after cell seeding.

Subsequently, cells were washed twice with PBS, fixed and permeabilized by addition of 100 µL of −20° C. cold methanol on ice for 20 minutes. Cells were washed twice with PBS and afterwards blocked with 5% fetal bovine serum and 5% bovine serum albumin in PBS (100 µL/well) at room temperature for 45 minutes. Finally, after an additional PBS washing step, the cells were stained with SGLT1 polyclonal antibody, ALEXA FLUOR® 647 conjugated (1:100 in PBS) or SLC7A5 polyclonal antibody, ALEXA FLUOR® 647 conjugated (1:200 in PBS) over night at 4° C. (50 µL/well).

In brief: On day 5 the cells were incubated overnight with the above described

Differentiation Medium which contained the test substances A, B and the combination thereof. In a first step, the effective dose range was identified by adding the phytogenic feed additives. The components A and B were supplemented in the following concentrations:

Essential oil mixture: 3.6, 7.3, 14.5, 21.8, 54.4, 109, 218, 544 mg/L

*Quillaja* saponins: 3.8, 7.6, 15.3, 23.0, 57.5, 115, 230, 575 mg/L

The highest concentration of the phytogenic substances thereby exactly corresponded to the dietary supplementation levels of 21.8 mg/kg (essential oils) and 23.0 mg/kg (saponins), respectively. Depending on the experiment the cells were then incubated with the first antibody anti-SGLT1 (dilution 1:50) or anti-PEPT1 (1:100) for 3 hours. After washing the plates five times with MEM, the cells were incubated with the ALEXA-fluor-coupled secondary antibody to anti-SGLT1 and anti-PEPT1. After washing the cells five times with MEM the abundance of SGLT1 and PET1, recruited to the cytoplasma membrane was studied with total internal reflection fluorescence microscopy.

Total Internal Reflection Fluorescence (TIRF)

The detection system was set up on an epi-fluorescence microscope (Olympus IX81). A diode laser (Toptica Photonics, Munich, Germany) was used for selective fluorescence excitation of Alexa647 at 640 nm. Samples were illuminated in total internal reflection (TIR) configuration (CellTIRF, Olympus) using a 60× oil immersion objective (NA=1.49, APON 60XO TIRF, Olympus, Munich, Germany). After appropriate filtering using standard filter sets, fluorescence was imaged onto a CCD camera (Orca-R2, Hamamatsu, Japan). Samples were mounted on an x-y-stage (CMR-STG-MHIX2-motorized table; Marzhauser, Germany) and scanning of larger areas was supported by a laser-guided automated focus-hold system (ZDC-2; Olympus).

Data Analysis

Initial imaging recordings were supported by the Olympus XcellenceRT software. Images were exported as TIRF-frames and fluorescence intensity analysis was performed using the Spotty framework (Borgmann et al., 2012).

Evaluation of the Effective Dose Range

Figure 1:
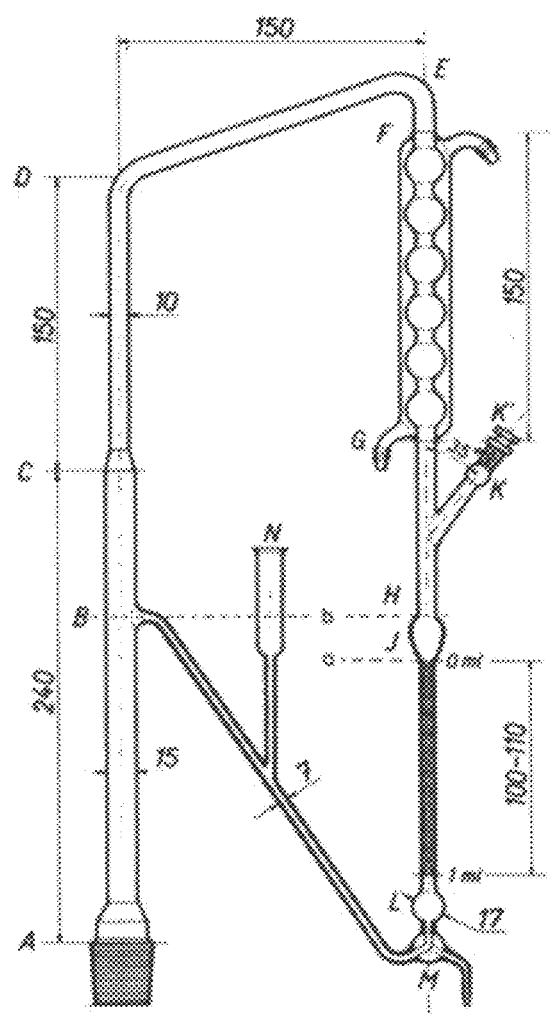
FIG. 1: Apparatus for determining essential oils in drugs
Figure 2:
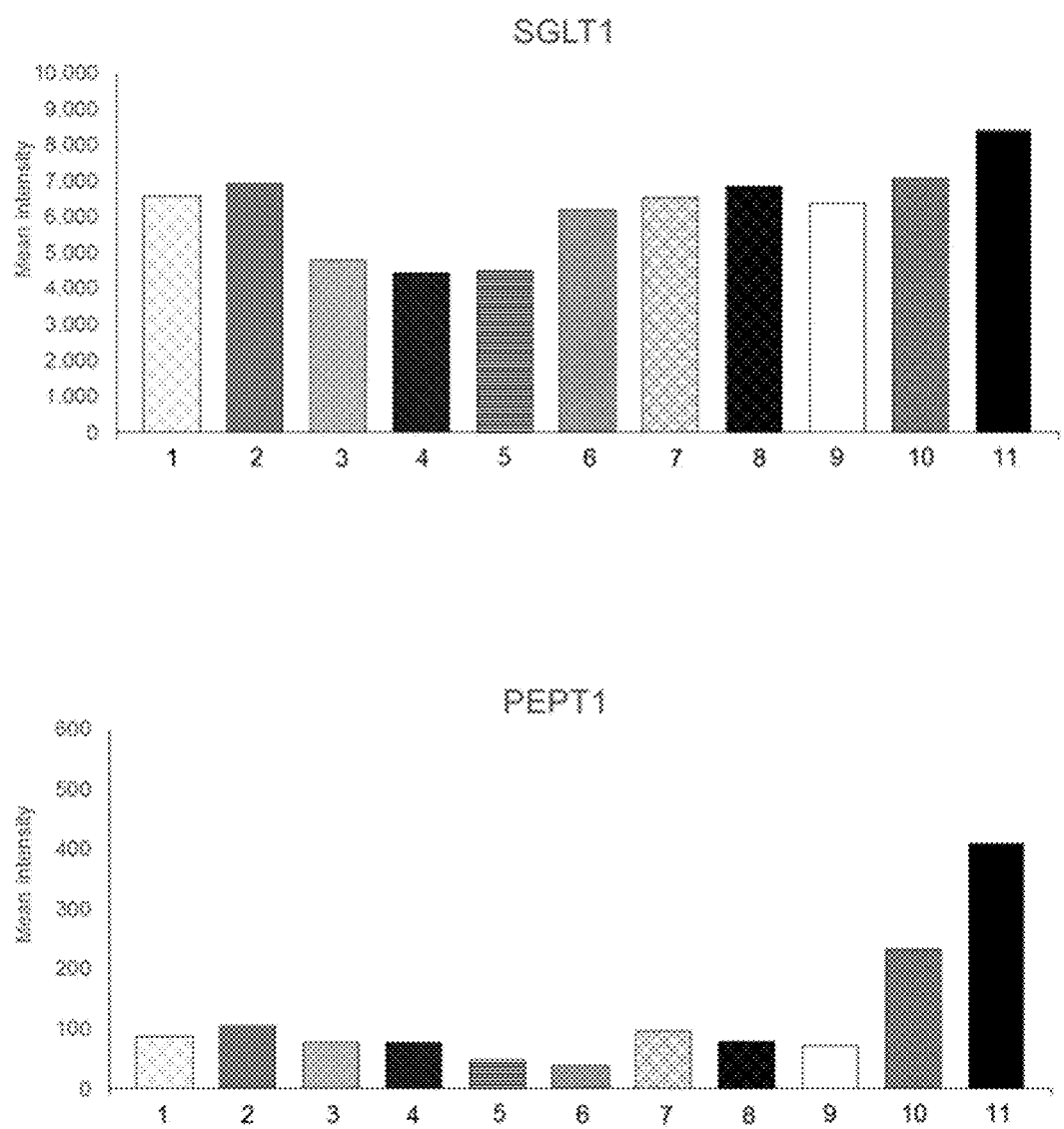
FIG. 2: dose-depending effect of the essential oil component A on membrane recruitment of sodium-dependent glucose transporter SGLT1 and di- and tripeptide Description of bars.

For both components, the concentration up to 2.5-fold the dietary dose level, no effect on the membrane recruitment of SGLT1 and PEPT1 in CaCo2 cells was documented. Whereas a concentration of 50-fold the dietary dose level showed cell-toxic effects on CaCo2-cells for both components. Results are given in FIG. 2 and FIG. 3. These results clearly showed that the CaCo2 model is principally suitable to study the effects of phytogenic substances on the membrane recruitment of nutrient transporters.

Membrane Recruitment and mRNA Expression

Starting with the above mentioned results as the basis, in the following experiments SGLT1 and PEPT1 membrane recruitment and gene expression were studied with component A, B and the combination thereof A+B (AB), at concentrations in the range equivalent to the 5,0-fold to 25-fold of the recommended dietary concentrations. Consequently, the new range for essential oils and saponins included concentrations from 115 mg/L to 575 mg/L.

Essential oils (A) showed no clear dose response on the recruitment of both nutrient transporter SGLT1 and PEPT1 (FIGS. 4 and 5). Between 0 mg/L and 115 mg/L, component A slightly increased the membrane recruitment of both SGLT1 and PEPT1 about 1.4-fold. Higher concentrations did not result in a further increase in recruitment.

In contrast to the essential oils, the saponin component B showed a more pronounced dose depending membrane recruitment on SGLT1, and in particular on PEPT1. Regarding SGLT1 recruitment, an increase was observed between 0 and 115 mg/L and between 115 and 173 mg/L before a plateau level was reached at higher concentrations up to 575 mg/L. Saponins clearly caused an uncontrovertible dose-response over the whole concentration range investigated. (FIGS. 4 and 5).

The combination of both components AB did not show any additional effects on SGLT1 recruitment, compared to component B, whereas a surprising further increase membrane recruitment of PEPT1 was clearly documented (FIGS. 4 and 5).

Regarding the mRNA expression of both nutrient transporter SGLT1 and PEPT1, a supplementation of only the essential oil component A to the tissue culture media remained without an effect. In contrast, the saponin component B caused a clear and uncontrovertible dose-response regarding the mRNA expression of both transporters. The supplementation of both components AB to the tissue culture media of the CaCo2 cells showed a surprisingly increased effect regarding SGLT1 expression, whereas, compared the supplementation on solely the saponin component B, no further increase of the on PEPT1 expression was found. Results are given in FIGS. 4 and 5.

Conclusion

The CaCo2 model is a suitable to study both, the membrane recruitment and the gene expression of nutrient transporters. In particular, saponins possess a distinct effect on the gene expression and the membrane recruitment of SGLT1 and PEPT1. Essential oils unexpectedly support and increase the saponin effects regarding PEPT1 membrane recruitment and regarding SGLT1 expression. For this purpose, the combination of essential oils and saponins seems to be meaningful with regard to nutrient absorption.

6. In Vivo Validation of Nutrient Transport Systems of the Brush Border Membrane and its Relevance for Animal Performance a. Ileal Nutrient Digestibility in Broilers In order to validate the relevance of the beneficial effects on the nutrient transport system found in vitro, an in vivo trial was carried out to evaluate the effect of the essential oil component A, the saponin component B and the combination thereof AB on ileal nutrient digestibility in broilers. The components A, B and AB were ad-mixed to commercial antibiotic-free broiler starter diets. The trial design is described in Table 2 below. In addition, tissue samples were taken from this trial to evaluate possible molecular mechanisms, using Microarray Technology, analyzing the differential gene expression patterns in the jejunum and the liver of birds.

TABLE 2

| Overview of experimental design | | | | | |
|---|---|---|---|---|---|
| Treatment group | | 0-control | A | B | AB |
| Essential oil component in the additive | mg/kg | — | 12.5 | — | 12.5 |
| Saponin component in the additive | mg/kg | — | — | 23 | 23 |
| Total birds per group | No | 32 | 32 | 32 | 31 |
| Repetitions | No | 9 | 9 | 9 | 9 |

Diets and Feeding Regime

The essential oil component A, the saponin component B and the combination thereof AB, were ad-mixed to antibiotic-free commercial broiler starter diets, based on corn, soybean meal and wheat, iso-caloric and iso-nutritive and meeting the nutritional requirements of growing broiler chickens as recommended by the Society of Nutrition Physiology (1999). During the whole 21 d experimental period, diets were provided ad libitum and in mash form. Diets were prepared without the inclusion of any enzymes, growth promoters, antibiotics or coccidiostats.

Animals and Husbandry

A total number of 127 one-day old male Cobb 500 broiler chicken were randomly assigned to the 4 experimental groups with 36 birds per group (Table 2). The 36 birds of each experimental group were distributed to 9 cages with 4 birds each (9 repetitions per group). The duration of the feeding period was 21 days. The stainless steel cages with a base area of 0.19 m2 (=34 cm×55 cm) are positioned in a climated experimental room. In the first two weeks of the experiment the room temperature is kept at 25° C., and it is reduced in the third week to 23° C. Lighting duration is 24 hours during the first 3 days and 18 hours from day 4 onwards. Humidity is adjusted to 65%. The birds have free access to tap water and the individual diets, provided as a "feed-flour".

Ileal Nutrient Digestibility

Heal nutrient digestibility was analyzed for 27 birds of each experimental group on day 21. For this purpose the birds were killed on day 21, 2 hours after starting the lighting cycle. The complete ileum (start: Meckel's diverticulum, end: 3 cm cranial to the ostium ileocaecale) was resected. Ileal chymus was collected by purging the ileum with a defined amount (5 to 10 mL) of water or physiological sodium chloride solution. The ileal contents of the 3 birds of one cage were pooled. The concentration of organic matter, crude protein, crude lipids, crude ash, calcium, and phosphorus in the pooled ileal digesta and in the diets was analyzed, precaecal digestibility of the mentioned nutrients is calculated from the analysed nutrient concentration in the diet and digesta. The results are given in Table 3 below.

TABLE 3

| Effect of the component A, B and AB on ileal nutrient digestibility in broilers at day 21 of age. | | | | | | |
|---|---|---|---|---|---|---|
| Treatment group | | Control | A | B | AB | P value |
| Body weight | kg | 794.8 ± 53.0 | 819.6 ± 58.9 | 826.3 ± 52.5 | 813.5 ± 24.4 | 0.610 |
| Ileal digesta | | | | | | |
| Dry matter | % | 52.54 ± 2.20 | 51.76 ± 4.68 | 49.95 ± 3.27 | 52.80 ± 5.47 | 0.617 |
| Ileal digestibility | | | | | | |
| Crude ash | % | 42.33 ± 4.08 | 44.56 ± 2.65 | 45.57 ± 0.88 | 46.71 ± 3.69 | 0.061 |
| Crude protein | % | 80.76 ± 2.28$^a$ | 83.10 ± 1.20$^b$ | 83.16 ± 1.41$^b$ | 83.97 ± 1.47$^b$ | <0.001 |
| Crude fat | % | 97.70 ± 0.17 | 97.49 ± 1.13 | 97.28 ± 0.61 | 97.66 ± 1.30 | 0.908 |
| Calcium | % | 42.53 ± 4.65 | 45.14 ± 2.52 | 45.15 ± 3.60 | 44.68 ± 2.05 | 0.229 |
| Phosphorus | % | 51.28 ± 5.31 | 53.60 ± 3.52 | 53.17 ± 4.20 | 53.03 ± 3.41 | 0.915 |

According to the significantly increased ileal crude protein digestibility, also significant changes in the digestibility of numerous non essential and essential amino acids could be analysed in all groups receiving diets with added phytogenic feed additives compared to control animals (Table 4).

TABLE 4

| Effect of the component A, B and AB on ileal digestibility of amino acids in broilers at day 21 of age. | | | | | | |
|---|---|---|---|---|---|---|
| Treatment group | | Control | A | B | AB | P value |
| Ileal digestibility | | | | | | |
| Crude protein | % | 80.76 ± 2.28$^a$ | 83.10 ± 1.20$^b$ | 83.16 ± 1.41$^b$ | 83.97 ± 1.47$^b$ | <0.001 |
| Alanine | % | 79.03 ± 2.53$^a$ | 80.94 ± 2.09$^{ab}$ | 81.76 ± 1.95$^{ab}$ | 83.13 ± 2.56$^b$ | 0.013 |
| Arginine | % | 88.29 ± 1.52$^{ab}$ | 90.80 ± 3.17$^c$ | 89.03 ± 1.42$^{abc}$ | 90.75 ± 1.03$^{bc}$ | 0.004 |

TABLE 4-continued

Effect of the component A, B and AB on ileal digestibility of amino acids in broilers at day 21 of age.

| Treatment group | | Control | A | B | AB | P value |
|---|---|---|---|---|---|---|
| Asparic acid | % | 78.55 ± 2.53 | 81.01 ± 1.37 | 80.35 ± 1.98 | 81.86 ± 1.75 | 0.112 |
| Cysteine | % | 71.64 ± 2.94 | 72.97 ± 2.36 | 70.50 ± 5.54 | 71.99 ± 4.28 | 0.335 |
| Glutamic acid | % | 82.59 ± 2.18$^a$ | 84.00 ± 0.97$^{ab}$ | 83.85 ± 1.67$^{ab}$ | 85.70 ± 1.55$^b$ | 0.027 |
| Glycine | % | 76.07 ± 2.61$^a$ | 78.36 ± 1.40$^{ab}$ | 78.22 ± 1.93$^{ab}$ | 80.06 ± 2.14$^b$ | 0.010 |
| Histidine | % | 85.28 ± 1.64 | 85.71 ± 1.77 | 84.58 ± 2.01 | 86.07 ± 1.66 | 0.069 |
| Isoleucine | % | 80.12 ± 2.43$^a$ | 83.73 ± 1.30$^{bc}$ | 81.92 ± 2.77$^{ab}$ | 85.56 ± 2.34$^c$ | <0.001 |
| Leucine | % | 82.62 ± 2.02$^a$ | 84.87 ± 0.95$^{ab}$ | 84.65 ± 1.75$^{ab}$ | 86.03 ± 1.93$^b$ | 0.002 |
| Lysine | % | 83.77 ± 1.88$^a$ | 86.78 ± 0.98$^{bc}$ | 85.62 ± 1.58$^{abc}$ | 87.20 ± 1.79$^c$ | <0.001 |
| Methionine | % | 94.05 ± 1.65$^a$ | 92.46 ± 2.04$^a$ | 91.50 ± 1.87$^{ab}$ | 85.52 ± 11.73$^b$ | 0.004 |
| Phenylalanine | % | 85.25 ± 1.87$^a$ | 87.08 ± 0.88$^{ab}$ | 86.79 ± 1.55$^{ab}$ | 88.08 ± 1.73$^b$ | 0.012 |
| Proline | % | 84.16 ± 1.98 | 84.77 ± 1.17 | 84.97 ± 1.64 | 85.50 ± 1.60 | 0.477 |
| Serine | % | 80.57 ± 2.53 | 82.62 ± 1.17 | 82.92 ± 1.72 | 83.66 ± 1.63 | 0.060 |
| Threonine | % | 74.65 ± 3.29 | 78.04 ± 1.63 | 77.10 ± 2.18 | 78.45 ± 2.49 | 0.070 |
| Tyrosine | % | 77.24 ± 3.98$^{ab}$ | 80.89 ± 1.55$^b$ | 79.63 ± 2.11$^{ab}$ | 80.28 ± 2.13$^b$ | 0.001 |
| Valine | % | 76.74 ± 2.61$^a$ | 80.94 ± 2.09$^{bc}$ | 79.41 ± 2.75$^{abc}$ | 83.13 ± 2.56$^c$ | <0.001 |
| Total amino acids | % | 81.04 ± 2.19 | 83.19 ± 1.10 | 82.55 ± 1.91 | 83.87 ± 1.87 | 0.085 |

$^{ab}$Values with different superscripts within lines differ significantly (P < 0.05).

Conclusion

From the results it can be concluded that the combination of the essential oil component A and the saponin component B showed statistically positive effects on ileal digestibility of proteins in broiler chickens. The beneficial effect of AB on the ileal digestibility of protein corresponds to the results of the in vitro model described above.

b. Evaluation of Metabolic and Signaling Pathway in Liver and Jejunum

Microarray Analysis of Differential Gene Expression in the Jejunum and the Liver Regarding the transcriptional level, the comparisons of dietary groups with untreated control solely revealed differences in transcript abundances between saponin component B and an untreated control group. Consequently, a set of 613 and 610 genes were considered for analyses in liver and jejunum, respectively. In the background of metabolism and signaling, most prominent tissue-specific canonical pathways are listed in Table 5. In general, signaling pathways showed higher significance levels compared to metabolic pathways.

TABLE 5

Saponin feeding induced changes in metabolic and signaling pathways, obtained from Ingenuity Pathway Analysis, following differential expression in the liver and the jejunum (B > CON).

| Canonical pathway | Tissue | p-value | Number of assigned molecules |
|---|---|---|---|
| Metabolic pathways | | | |
| Superpathway of Inositol Phosphate Compounds | Liver | 9.03E−03 | 15 |
| Oxidative Phosphorylation | Liver | 1.44E−02 | 10 |
| 3-phosphoinositide Biosynthesis | Jejunum | 7.84E−03 | 13 |
| Heme Biosynthesis II | Jejunum | 2.86E−02 | 3 |
| Signaling pathways | | | |
| Erythropoietin Signaling | Liver | 1.43E−04 | 12 |
| Germ Cell-Sertoli Cell Junction Signaling | Liver | 1.20E−03 | 18 |
| EIF2 Signaling | Jejunum | 2.84E−04 | 18 |
| Integrin Signaling | Jejunum | 3.71E−04 | 21 |

To get insight into the effects of transcriptional differences related to saponin supplementation, biofunctions with predicted activation scores of particular IPA-categories were analysed. In liver, functional categories were selected with respect to their relationship to energy metabolism ('Carbohydrate metabolism', 'Lipid metabolism' and 'Free radical scavenging'). In jejunum, selected functional categories pertained to nutrient absorption and cellular interaction ('Cell-To-Cell Signaling and Interaction' and 'Molecular Transport').

Regarding the biofunctions assigned to 'Carbohydrate metabolism' the highest Z-scores were obtained for 'Clearance of D-glucose' (1.131), 'Synthesis of D-glucose' (−0.896) and 'Synthesis of monosaccharide' (−0.788). In the functional category of 'Lipid metabolism', the biofunctions related to conversion and storage were consistently predicted to be inactivated in the saponin group compared to the control group. Biofunctions referring to the production of reactive oxygen species and superoxide showed elevated Z-scores related to inactivation of these functions in liver tissue (B>CON).

Regarding the biological process category of 'Cell-To-Cell Signaling and Interaction', the biofunction related to adhesion was predicted to be significantly activated in jejunum of saponin treated animals compared to controls. Additionally, activation prediction revealed consistent activating effects on transport and uptake of protein, glucose and fatty acid for the comparison of saponin and control group.

With respect to reported biofunctions, transcriptional differences of all three treatment groups compared to control group were analyzed. Regarding the functional categories of 'Lipid metabolism' and 'Cell-to-cell signaling and interaction', the set of selected genes was based on predicted activated biofunctions (Table 6) obtained for the comparison of B>CON.

TABLE 6

Enriched IPA-biofunctions with predicted activation states (Z-score) of selected functional IPA-categories (B > CON).

| Tissue | Category | Function | Function Annotation | p-value | Z-score | # Molecules |
|---|---|---|---|---|---|---|
| Liver | Carbohydrate Metabolism | clearance | clearance of D-glucose | 8.41E−03 | 1.131 | 5 |
| | | synthesis | synthesis of D-glucose | 3.25E−02 | −0.896 | 8 |
| | | synthesis | synthesis of monosaccharide | 8.14E−03 | −0.788 | 10 |
| | | transport | transport of 2-deoxyglucose | 4.10E−03 | 0.174 | 7 |
| | | transport | transport of D-glucose | 2.21E−02 | 0.115 | 15 |
| | | transport | transport of monosaccharide | 2.87E−02 | 0.606 | 16 |
| | | uptake | uptake of 2-deoxyglucose | 9.20E−03 | 0.308 | 13 |
| | Lipid Metabolism | conversion | conversion of lipid | 3.78E−02 | −0.642 | 15 |
| | | storage | storage of cholesterol | 8.41E−03 | −0.447 | 5 |
| | | storage | storage of lipid | 1.86E−03 | −0.277 | 12 |
| | Free Radical Scavenging | metabolism | metabolism of ROS | 1.45E−03 | −0.610 | 49 |
| | | production | production of ROS | 9.98E−03 | −0.692 | 34 |
| | | production | production of superoxide | 3.06E−02 | −1.851 | 11 |
| | | synthesis | synthesis of ROS | 1.85E−03 | −0.556 | 47 |
| Jejunum | Cell-To-Cell Signaling and Interaction | adhesion | adhesion of tumor cell lines | 2.51E−02 | 2.491 | 23 |
| | | attachment | attachment of tumor cell lines | 3.01E−02 | 0.447 | 6 |
| | | excitation | excitation of neurons | 1.09E−02 | −1.342 | 7 |
| | Molecular Transport | mobilization | mobilization of Ca2+ | 2.91E−02 | −0.288 | 21 |
| | | quantity | quantity of adiponectin | 1.09E−02 | 0.152 | 4 |
| | | transport | transport of protein | 3.75E−02 | 1.446 | 26 |
| | | uptake | uptake of D-glucose | 9.87E−03 | 1.426 | 22 |
| | | uptake | uptake of fatty acid | 1.33E−02 | 1.634 | 9 |

Genes assigned to the category of 'Lipid metabolism' are involved in regulation and transduction of processes related to conversion and storage of lipids Table 7. Transcript abundances of genes affecting hepatic beta oxidation and storage of fatty acids were decreased (e.g. APOB, CROT and LPL), whereas transcripts mediating signal transduction were enriched in B compared to CON (e.g. FFAR2 and NFKBIA). The expression patterns of transcripts were highly consistent over all three comparisons, but sparely reached significant differences in contrasts other than B>CON.

TABLE 7

Fold change of gene-set assigned to lipid metabolism in the liver. Columns indicate comparisons of different dietary treatment groups, namely Essential oils + Saponins (AB), Essential oils (A) and Saponins (B) with control group.
Lipid metabolism

| | Fold change | | |
|---|---|---|---|
| Gene | A | B | AB |
| APOB | −1.19 | −1.49 * | −1.24 |
| CAT | −1.23 | −1.46 * | −1.23 |
| CD36 | −1.11 | −1.48 * | −1.13 |
| CROT | −1.33 | −1.55 * | −1.33 |
| CRY1 | −1.17 | −1.64 * | −1.17 |
| CYP2D6 | −1.12 | −1.39 * | −1.12 |
| DECR2 | 1.28 | 1.55 * | 1.28 |
| FFAR2 | 1.10 | 1.55 * | 1.10 |
| HPGD | −1.09 | −1.64 * | −1.09 |
| HTT | −1.25 | −1.51 * | −1.25 |
| ITGAV | −1.22 | −1.36 * | −1.22 |
| LCLAT1 | −1.13 | −1.28 * | −1.13 |
| LPL | −1.55 * | −1.57 * | −1.55 * |
| MAP4K4 | −1.05 | −1.39 * | −1.05 |
| MAPK9 | −1.18 | −1.49 * | −1.18 |
| NFKBIA | 1.37 | 1.65 * | 1.37 |
| NR1H4 | −1.31 | −1.53 * | −1.31 |

TABLE 7-continued

Fold change of gene-set assigned to lipid metabolism in the liver. Columns indicate comparisons of different dietary treatment groups, namely Essential oils + Saponins (AB), Essential oils (A) and Saponins (B) with control group.
Lipid metabolism

| | Fold change | | |
|---|---|---|---|
| Gene | A | B | AB |
| NR1P4 | −1.32 | −1.79 * | −1.32 |
| OSBPL8 | −1.17 | 1.67 * | −1.17 |
| PPARG | −1.36 | −1.96 * | 1.36 |
| PTEN | −1.17 | −1.43 * | −1.17 |
| PTEN2 | −1.27 | −1.56 * | −1.27 |
| SREBF2 | 1.22 | 1.44 * | 1.22 |
| TECR | −1.54 | −2.11 * | −1.54 |
| TTPA | −1.11 | −1.45 * | −1.11 |
| TXN2 | 1.06 | 1.35 * | 1.06 |

Asterisk indicates significant differences in transcript abundance compared to control (p ≤ 0.05).

In jejunum, the analyses of transcripts assigned to 'Cell-to-cell signaling and interaction' revealed distinct group specific differences (e.g. AKT1, CD47 and EGR1) (Table 8). Consistent and also significant differences over all three comparisons were obtained, as depicted for ADDS, ARHGAP21, MYH9 and VEGFA. Genes with function in cellular association and interaction including TJP1 and LAMAS showed elevated transcript abundance in treatment groups compared to control group.

TABLE 8

Fold change of gene-set assigned to "Cell-to-Cell signaling" in the jejunum. Columns indicate comparisons of different dietary treatment groups, namely Essential oils + Saponins (AB), Essential oils (A) and Saponins (B) with control group.
Cell-to-cell signaling and interaction

| Gene | Fold change | | |
|---|---|---|---|
| | A | B | AB |
| ADD3 | −2.02 * | −1.83 * | 1.93 * |
| AKT1 | 1.03 | 1.18 * | 1.16 * |
| ARHGAP21 | 1.36 * | 1.67 * | 1.26 * |
| C1QBP | −1.31 | −1.64 * | −1.39 |
| CD47 | 1.05 | 1.18 * | −1.06 |
| DBF4 | −1.04 | 1.28 * | −1.02 |
| DSG2 | 1.14 | 1.44 * | 1.28 |
| EGR1 | 1.30 * | 1.18 * | −1.07 |
| FGF19 | 1.19 | 1.67 * | 1.36 |
| FOS | 2.10 * | 2.14 * | 1.80 |
| ILK | −1.06 | −1.31 * | −1.08 |
| ITGA6 | 1.06 | 1.43 * | 1.20 |
| LAMA3 | 1.07 | 1.38 * | 1.13 |
| MGAT5 | 1.11 | 1.28 * | 1.13 * |
| MYH9 | 1.25 * | 1.52 * | 1.20 * |
| NFKBIA | 1.22 | 1.44 * | 1.02 |
| PPARG | 1.05 | 1.41 * | 1.10 |
| RAC1 | 1.26 * | 1.34 * | 1.09 |
| ROCK2 | 1.08 | 1.96 * | 1.32 |
| SACM1L | 1.04 | 1.19 * | 1.06 |
| TJP1 | 1.02 | 1.31 * | 1.19 |
| VEGFA | 1.79 * | 1.93 * | 1.56 * |
| VEGFC | 1.01 | 1.27 * | 1.14 |

Asterisk indicates significant differences in transcript abundance compared to control ($p \leq 0.05$).

The set of genes selected for the category of 'Carbohydrate metabolism' was driven by the role of genes in regulation of carbohydrate metabolism and their significant enrichment in the comparison of B>CON. In liver tissue, increased transcript abundance was obtained for key regulators of glycolysis and gluconeogenesis, namely PCK2, PFKFB4, PFKL and PKM2 (Table 9). Additionally, comparison of A>CON and AB>CON revealed consistent although not significant differences for mRNA levels of these key regulatory enzymes. In general, expression patterns implicate overlapping effects on carbohydrate metabolism for all treatment groups compared to control.

TABLE 9

Fold change of gene-set assigned to carbohydrate metabolism in the liver. Columns indicate comparisons of different dietary treatment groups, namely Essential oils + Saponins (AB), Essential oils (A) and Saponins (B) with control group.
Carbohydrate metabolism

| transporter | Fold change | | |
|---|---|---|---|
| | A | B | AB |
| PKM2 | 1.24 | 1.56 * | 1.24 |
| PFKFB4 | 1.10 | 1.42 * | 1.07 |
| PFKL | 1.33 | 1.75 * | 1.25 |
| TPI1 | 1.11 | 1.27 * | 1.19 * |
| MPI | 1.19 | 1.46 * | 1.30 * |
| SLC2A2 | 1.37 * | 1.39 * | 1.14 |
| Galk1 | 1.31 | 1.57 * | 1.29 |
| PCK2 | 1.41 | 1.71 * | 1.23 |

Asterisk indicates significant differences in transcript abundance compared to control ($p \leq 0.05$).

Regarding the 'Molecular transport' category, the differential abundance of transcripts with focus to peptide and amino acid transport was investigated. Expression profiles of genes encoding for the selected solute carrier proteins were consistently increased in the B>CON comparison (Table 10). Highest fold changes of mRNA abundance was obtained for neutral amino acid transporters SLC38A2 and SLC6A19. Significant differences in transcript abundance mainly overlapped for groups fed with saponin component (B>CON and AB>CON).

TABLE 10

Fold change of gene-set assigned to "peptide and amino acid transporters" in the jejunum. Columns indicate comparisons of different dietary treatment groups, namely Essential oils + Saponins (AB), Essential oils (A) and Saponins (B) with control group.
Peptide and amino acid transporters

| transporter | Fold change | | |
|---|---|---|---|
| | A | B | AB |
| SLC6A19 | 1.22 | 1.69 * | 1.36 * |
| SLC1A1 | 1.07 | 1.41 * | 1.21 |
| SLC15A1 | 1.24 | 1.49 * | 1.46 * |
| SLC38A2 | 1.20 | 2.02 * | −1.07 |
| SLC38A3 | 1.43 * | 1.43 * | 1.21 |
| SLC7A6 | 1.13 | 1.50 * | 1.19 * |
| SLC38A9 | −1.02 | 1.25 * | 1.06 |

Asterisk indicates significant differences in transcript abundance compared to control ($p \leq 0.05$).

c. Feed Conversion Efficiency in Broilers

To evaluate the relevance of observed effects on nutrient digestibility and nutrient transport systems on feed efficiency of broilers, the essential oil component A, the saponin component B and the combination thereof AB, were ad-mixed to commercial broiler diets. The experimental design is described in Table 11. Growth performance and feed intake of broiler chicken were monitored from day 1 to day 42 of age.

TABLE 11

Overview of experimental design

| Treatment group | | 0-control | A | B | AB |
|---|---|---|---|---|---|
| Essential oil component in the additive | mg/kg | — | 12.5 | — | 12.5 |
| Saponin component in the additive | mg/kg | — | — | 23 | 23 |
| Total birds per group | no | 120 | 120 | 120 | 120 |
| Repetitions | no | 6 | 6 | 6 | 6 |

Diets and Feeding Regime

The essential oil component A, the saponin component B and the combination thereof AB, were ad-mixed to commercial antibiotic-free broiler diets via premixtures at a level of 1,000 mg/kg feed. The dietary levels of the experimental diets and the analysis of the components A and B are given in Table 12 rsp. Table 13 below. During the 42 d experimental period two feeding phase diets, based on corn, soybean meal and wheat, were provided in mash form from 01 to 21 days (starter diet) from 22 to 42 days of age (finisher diet), iso-caloric and iso-nutritive and meeting the nutritional requirements of growing broiler chickens as recommended by the Society of Nutrition Physiology (1999). Diets were prepared without the inclusion of any enzymes, growth promoters, antibiotics or coccidiostats.

TABLE 12

Analysed nutrient composition (g/kg) in the diets of the single experimental groups

| Parameter | | Control | A | B | AB |
|---|---|---|---|---|---|
| Dry matter | g/kg | 904.2 | 906.7 | 902.1 | 903.8 |
| Crude protein | g/kg | 221.8 | 221.7 | 222.0 | 221.5 |
| Crude fibre | g/kg | 38.4 | 36.9 | 38.0 | 37.2 |
| Crude fat | g/kg | 97.0 | 96.7 | 95.3 | 96.2 |
| Crude ash | g/kg | 58.4 | 58.0 | 58.2 | 58.4 |
| Starch | g/kg | 320.2 | 318.6 | 319.2 | 318.4 |
| Sugars | g/kg | 42.9 | 42.7 | 43.6 | 43.0 |
| Calcium | g/kg | 9.0 | 9.0 | 9.1 | 9.0 |
| Phosphorus | g/kg | 7.0 | 7.1 | 6.8 | 7.0 |
| Sodium | g/kg | 1.6 | 1.7 | 1.6 | 1.6 |

TABLE 13

Foam index analysed in premix, and thymol analysed in complete diets

| Parameter | | Expected | Control | A | B | AB |
|---|---|---|---|---|---|---|
| Foam index in premix | cm | 2.1 | — | | 1.9 | 2.0 |
| Thymol concentration in complete diet | mg/kg | 1.0 | — | 1.0 | — | 1.1 |

Animals and Husbandry

Four hundred and eighty one-day-old healthy male broiler chicken (Cobb 500) were allocated to 24 pens (3.1 m$^2$) with bedding of softwood shaving. Chicken were sexed and vaccinated at the hatchery. The poultry house was equipped with controlled climate and forced ventilation (air speeds from 0.3 (1 to 18 days of age) up to 1.0 m/s from 19 days of age onwards). Ambient temperature was gradually reduced from 32° C. at day 1 of age to about 28° C. at day 21 of age. The relative humidity was controlled to be within 50 and 65%. The light (45 lux) during the first 4 days of age was provided for 24 h continuously. From day 5 of age onwards, the daily light (45 lux) was reduced to 18 h. Feed and fresh water was continuously supplied ad libitum.

Productive Performance

Productive performance (body weight, body weight gain, feed intake and feed conversion ratio) was measured per pen (replicate unit) from 1 to 42 days of age. For calculation of the body weight gain per broiler chicken the following formula was used:

Average weight gain per bird for each period →F−S (corrected by weight gain of died or culled chickens)

F—Average weight of the live birds in the pen at the weighing day

S—Average weight of the live birds in the pen at the previous weighing

The feed intake (corrected for dispersed feed) is calculated by using the following formula:

$$\text{Feed intake per period} = \frac{\text{total feed consumed per pen}}{\left(\begin{array}{c}\text{number of surviving birds} \times \\ \text{days of the period}\end{array}\right) + \text{days of died birds alive}}$$

The feed conversion ratio is estimated by using the following formula:

$$\text{Feed conversion per period} = \frac{\text{total feed consumed for the period in each replicate}}{\text{total weight gain for the period}}$$
(with gain of died or culled chickens)

Statistical Analysis

The statistical analysis of the experimental data was performed with the statistics program SAS. The data are presented as means±standard deviation (SD). Significant differences between means (P<0.05) were evaluated with the LSD-test.

Results

Body Weight Development

The growth rate of all groups was within the normal performance given by the breeder. The details of body weight development are given in Table 14 below. After 21 days the body weight of birds that received the combination AB was 2.3% above the control. While the body weight of the treatment group AB was significantly improved compared to the untreated control, the supplementation with only single components A or B, did not increase body weight of birds until day 21 of age. During the finisher period from day 21 to day 42 of age, this difference in body weight between the treatments increased. After 42 days, all treatment groups showed significant improvement in body weight compared to the untreated control. A supplementation of the essential oil component increased the body weight by 3.5% and the saponin component B by 4.3%, compared to the control. The combination AB significantly improved the body weight by 5.3% compared to the control and by 1.9% compared to A.

TABLE 14

Effect of A, B and AB on body weight development of broilers

| Treatment group | | 0-control | A | B | AB |
|---|---|---|---|---|---|
| Total birds per group | no | 97 | 97 | 97 | 98 |
| Repetitions | no | 5 | 5 | 5 | 5 |
| Body weight, day 01 | g | 44.6 ± 1.0 | 44.6 ± 1.1 | 44.6 ± 0.5 | 44.6 ± 1.0 |
| Body weight, day 21 | g | 815.5 ± 9.1$^b$ | 803.0 ± 15.5$^b$ | 808.7 ± 9.7$^b$ | 834.4 ± 17.1$^a$ |
| Body weight, day 42 | g | 2799.9 ± 28.8$^c$ | 2898.3 ± 12.1$^b$ | 2921.4 ± 27.5$^{ab}$ | 2947.1 ± 43.0$^a$ |

Values in same column with no common superscript are significantly different (P ≤ 0.05)

Feed Intake

The overall feed consumption of birds fed the starter and finisher diet without supplementation of A, B or AB amounted to 3.69 kg per broiler chicken or 88.0 g per bird and day. With regard to the market weight at 42 days of age, comparable effects on feed intake between the treatments A and AB could be shown. The supplementation of A and AB to the control diets slightly increased the overall feed intake by 52 g and 33 g per bird over the whole period. The feed intake of broilers fed the diet supplemented with the saponin component B, showed to be significantly higher compared to the control by 3%.

Feed Conversion

The overall feed conversion (kg feed per kg body weight gain) during the 42-day-feeding period for broilers fed starter and finisher diets without supplementation of A, B or AB added up to 1.34 g/g. The supplementation of saponin component B only slightly improved the feed conversion to 1.32 g/g. The essential oil component A statistically improved the feed conversion rate by 2.1%, whereas the combination AB statistically improved feed conversion by 4.3% to 1.28 g/g. Compared to the supplementation with single components A and B, the combination AB statistically improved feed conversion by 2.2% and 2.8% respectively.

TABLE 15

Effect of A, B and AB on productive performance of broilers (01 to 42 d of age)

| Treatment group | | 0-control | A | B | AB |
| --- | --- | --- | --- | --- | --- |
| Total birds per group | no | 97 | 97 | 97 | 98 |
| Repetitions | no | 5 | 5 | 5 | 5 |
| Body weight gain | g | 2755.3 ± 28.6$^c$ | 2853.7 ± 11.5$^b$ | 2876.8 ± 27.2$^{ab}$ | 2902.5 ± 42.8$^a$ |
| Feed intake | g | 3694.2 ± 37.9$^b$ | 3746.0 ± 55.0$^{ab}$ | 3803.0 ± 41.2$^a$ | 3727.5 ± 56.6$^b$ |
| Feed conversion | | 1.341 ± 0.017$^a$ | 1.313 ± 0.016$^b$ | 1.321 ± 0.013$^{ab}$ | 1.284 ± 0.025$^c$ |

Values in same column with no common superscript are significantly different (P ≤ 0.05).

Conclusion

From the results it can be concluded that the combination of the essential oil component A and the saponin component B showed statistically positive effects on performance of broiler chickens during the overall period of 42 days of age. The efficacy was mainly focussed on the reduction of feed amount per kg body weight gain. This effect was statistically higher than if the components A and B were supplemented alone and indicating synergistic effects for the combination AB.

The invention claimed is:

1. A method of improving feed conversion efficiency in antibiotic-free poultry production comprising administering to poultry animal a poultry feed additive composition which is a flowable mixture of phytogenic compounds comprising at least
   a. an oil component which is microencapsulated essential thyme oil, and
   b. particulate dried quillaja bark powder comprising a saponin component ranging from 3 to 10% (w/w quillaja bark powder),
   wherein the mixture contains at least 0.5% saponin component (w/w), and at least 0.2% (w/w) of the oil component per saponin component.

2. The method of claim 1, wherein an effective ratio of oil component to saponin component is in the range of 0.2:1 to 10:1.

3. The method of claim 1, wherein the composition comprises the oil component in an amount ranging from 0.2% to 5% (w/w), and the saponin component in an amount ranging from 0.5% to 5.0% (w/w).

4. The method of claim 1, wherein the composition further comprises one or more additional essential oils, dried herbs, spices and excipients, and optionally bulking and anti-caking agents.

5. The method of claim 4, wherein the additional essential oil is star anis oil.

6. The method of claim 1, wherein the oil component is prepared by spray-drying an o/w emulsion of the essential thyme oil.

7. The method of claim 1, wherein the composition is a storage stable, pelletable preparation, with a stability of at least 18 months at room temperature.

8. The method of claim 1, wherein the composition is provided in a feed product comprising the composition at a dose of at least 100 mg per kg feed product, optionally provided in the pelleted form.

9. The method of claim 1, wherein the feed conversion efficiency is determined by determining an Ileal nutrient digestibility or a feed conversion rate.

10. The method of claim 1, wherein the poultry feed additive is added to a poultry feed, to cause weight gain in poultry for laying and breeding.

11. A method of feeding a poultry animal with a feed product comprising administering with an antibiotic-free diet a poultry feed additive composition which is a flowable mixture of phytogenic compounds comprising at least
    a. an oil component which is microencapsulated essential thyme oil, and
    b. a saponin component which is the saponin contained in particulate dried quillaja bark powder,
    which mixture contains at least 0.5% saponin component (w/w), and the oil component in an effective ratio of at least 0.2:1 (w/w, oil component per saponin component), wherein said feed results in an improvement of the feed conversion efficiency.

12. The method according to claim 11, wherein said improvement results in an increase in average daily weight gain, of at least 2.0% over a period of 35 days, when the composition is dosed at an amount of at least 100 mg per kg feed product.

13. The method according to claim 11, wherein said improvement results in a decrease in the feed conversion ratio, of at least 2.5% over a period of at least 35 days, when the composition is dosed at an amount of at least 100 mg per kg feed product.

14. The method according to claim 11, wherein said improvement comprises results in an increased ileal protein digestibility, of at least 1% over a period of at least 35 days, when the composition is dosed at an amount of at least 100 mg per kg feed product.

15. The method of claim 1, wherein an effective ratio of oil component to saponin component is in the range of 1:1 to 5:1.

16. The method of claim 1, wherein an effective ratio of oil component to saponin component is in the range of 2:1 to 4:1.

* * * * *